(12) United States Patent
Cole

(10) Patent No.: US 9,724,007 B2
(45) Date of Patent: Aug. 8, 2017

(54) SYSTEM AND METHOD FOR DETECTING A CHARACTERISTIC IN AN ECG WAVEFORM

(75) Inventor: Bryan Thomas Cole, Allston, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 262 days.

(21) Appl. No.: 14/426,967

(22) PCT Filed: Sep. 11, 2012

(86) PCT No.: PCT/US2012/054620
§ 371 (c)(1),
(2), (4) Date: Mar. 9, 2015

(87) PCT Pub. No.: WO2014/042618
PCT Pub. Date: Mar. 20, 2014

(65) Prior Publication Data
US 2015/0190068 A1 Jul. 9, 2015

(51) Int. Cl.
*A61B 5/04* (2006.01)
*A61B 5/0452* (2006.01)
(Continued)

(52) U.S. Cl.
CPC ........ *A61B 5/04012* (2013.01); *A61B 5/0452* (2013.01); *A61B 5/0456* (2013.01);
(Continued)

(58) Field of Classification Search
CPC . A61B 5/04012; A61B 5/0456; A61B 5/0472; A61B 5/04; A61B 5/0468
(Continued)

(56) References Cited

U.S. PATENT DOCUMENTS 8,457,724 B2 * 6/2013 Zhang .................. A61B 5/0452
600/509

FOREIGN PATENT DOCUMENTS

WO WO-2008/007236 A2 1/2008
WO WO-2009/090581 A1 7/2009

OTHER PUBLICATIONS

International Search Report issued in PCT/US2012/054620 on May 31, 2013.
(Continued)

*Primary Examiner* — Christopher D Koharski
*Assistant Examiner* — Roland Dinga
(74) *Attorney, Agent, or Firm* — Jones Day (57) ABSTRACT

An apparatus and method is provided that identifies the presence or absence of a P-wave within a set of ECG data. A computation processor identifies the R-wave and then analyses a section of the waveform within a predetermined time window preceding the detected R-wave peak. The waveform within the window is analysed to identify a candidate P-wave, and in response to identifying the candidate P-wave a first and second feature associated therewith is measured. A composite feature value is calculated from the first and second measures, and compared to a classification threshold value. In an exemplary embodiment, the first feature represents a height between a highest peak of the candidate P-wave and a trough of the Q-wave, and the second feature represents a time between the peak of the candidate P-wave and a peak of the R-wave.

22 Claims, 9 Drawing Sheets

(51) Int. Cl.
  *A61B 5/0456* (2006.01)
  *A61B 5/0472* (2006.01)
  *A61B 5/00* (2006.01)
  *A61B 5/046* (2006.01)

(52) U.S. Cl.
  CPC ............ *A61B 5/0472* (2013.01); *A61B 5/046* (2013.01); *A61B 5/7246* (2013.01); *A61B 5/7264* (2013.01)

(58) Field of Classification Search
  USPC .................. 600/515, 516, 517, 518, 521
  See application file for complete search history.

(56) References Cited

OTHER PUBLICATIONS

Mao Ling et al. "P Wave Detection in ECG Signal Based on Location Estimation and Recognition Post-Processing", Signal Processing; Chinese Institute of Electronics; vol. 25, No. 6, Jun. 1, 2009: pp. 948-952.
Jonas Carlson et al. "Classification of Electrocardiographic P-Wave Morphology", IEEE Transactions on Biomedical Engineering. vol. 48, No. 4, Apr. 1, 2001.
Ken Freeman et al. "P Wave Detection of Ambulatory ECG," New Frontiers of Biomedical Engineering—Innovations From Nuclear to Space Technology: 13th Annual International Conference of the IEEE Engineering in Medicine and Biology Society: Oct. 31-Nov. 3, 1991, pp. 647-648.
Yogendra Narain Singh et al. "A Robust Delineation Approach of Electrocardiographic P Waves," 2009 IEEE Symposium on Industrial Electronics and Applications, Oct. 4, 2009: pp. 846-849.

\* cited by examiner

SYSTEM AND METHOD FOR DETECTING A CHARACTERISTIC IN AN ECG WAVEFORM

RELATED APPLICATION

This application is a national stage application, filed under 35 U.S.C. §371, of International Application No. PCT/US2012/054620 filed on Sept. 11, 2012, the contents of which are hereby fully incorporated by reference.

FIELD OF THE INVENTION

This invention concerns a system and method for analyzing cardiac electrophysiological signals to identify at least one characteristic associated with the electrophysiological signal for use in making decisions affecting cardiac medical treatment.

BACKGROUND OF THE INVENTION

Figure 1:
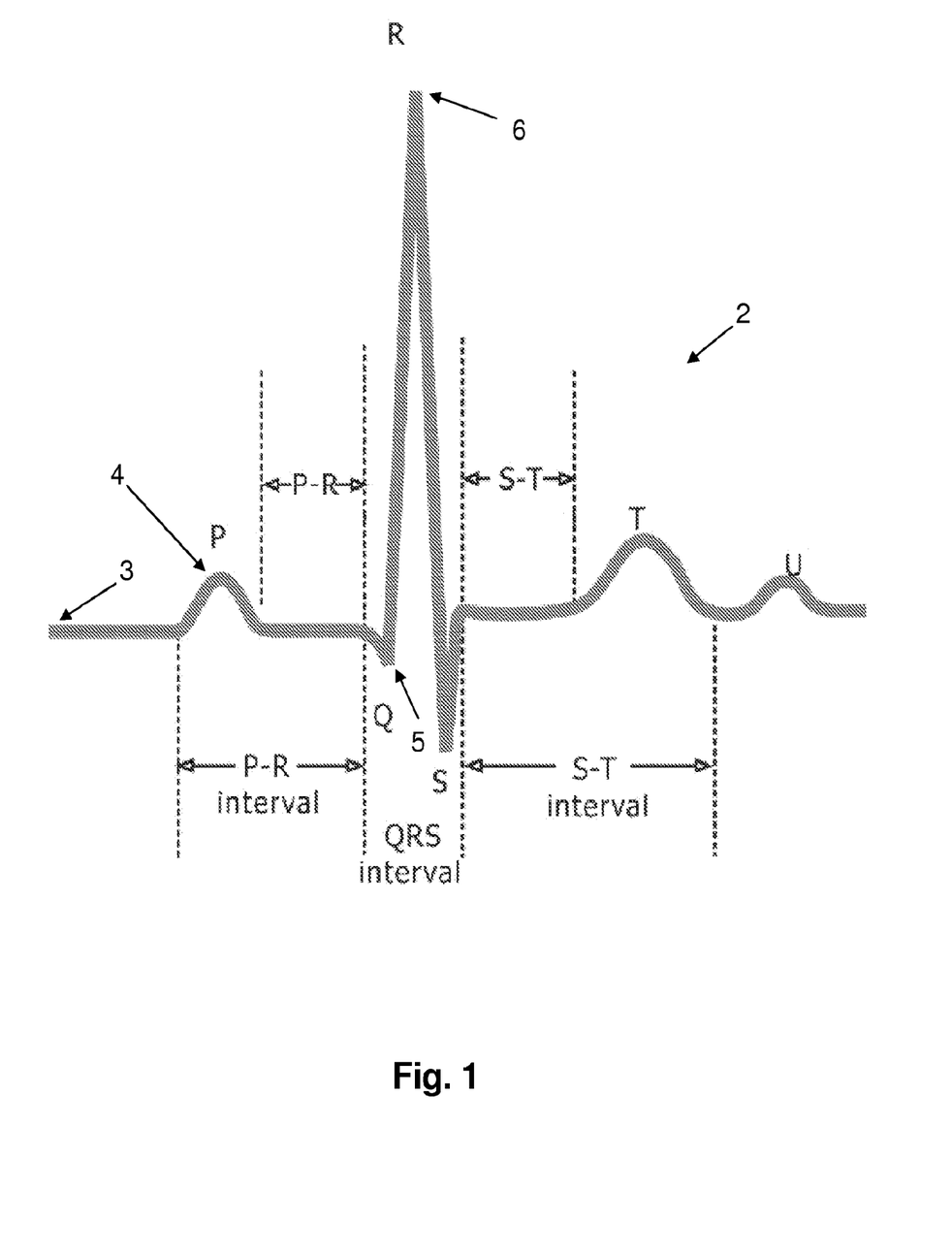
FIG. 1 is a prior art representation of an exemplary ECG waveform.

In the course of providing healthcare to patients, it is necessary to monitor vital statistics and other patient parameters. A plurality of different patient monitoring devices are able to selectively monitor the electrical impulses generated by a patient via at least one electrode coupled to the skin of the patient at particular locations on the body of the patient. For example, the electrical activity of the heart is routinely monitored in clinical environments using an electrocardiogram (ECG) monitor. The ECG monitor is connected to the patient by a plurality of electrodes that monitor the electrical impulses of the patient's heart. From electrophysiological signals sensed by the electrodes connected to the patient, the ECG monitor is able to generate an ECG waveform that includes data representing a series of successive heartbeats. An exemplary ECG waveform representing a single heartbeat 2 sensed by the electrodes is depicted in FIG. 1. The waveform 2 is formed from a plurality of different types of waves representing different electrical activities during a normal heartbeat and plotted against an isoelectric line 3 representing a base voltage. The waveform is comprised of a P wave, a QRS complex, a T-wave and, in some instances, a U-wave. The P wave represents atrial depolarization and includes a maximum amplitude represented by a peak 4. The QRS complex represents rapid depolarization of the right and left ventricles. Prior to depolarization, the Q point falls below the isoelectric line 3 and forms a trough 5. During depolarization of the ventricles, the maximum amplitude of the R point is the peak 6 thereof. The amplitude of peak 6 of the R point in the QRS complex is much greater than the amplitude of the peak 4 of the P wave due to the higher muscle mass generally associated with the ventricles as compared to the muscle mass of the atria. Following the QRS complex is the T wave which represents the repolarization of the ventricles during recovery. The U wave, if present, is believed to represent the repolarization of the septum between the left and right ventricles and follows in time having a maximum amplitude less than a maximum amplitude of the T wave.

From the different types of waves and complexes that form an ECG waveform, various features of the ECG waveform have been used to identify and classify various types of heartbeats for clinical use in diagnosing a medical condition of the patient. Common characteristics (or features) of ECG waveforms include any of the presence or absence of individual types of waves or complexes, the PR interval, the PR segment, the ST segment and the ST interval. Additionally, characteristics between successive heartbeats such as the RR interval representing a distance between successive R points have been used to detect certain cardiac conditions. A commonly detected cardiac condition is atrial fibrillation (AFIB). AFIB is a supraventricular tachyarrhythmia characterized by uncoordinated atrial activation with consequent deterioration of atrial mechanical function. On the surface electrocardiogram, AFIB is described by the replacement of consistent P waves by rapid oscillations or fibrillatory waves that vary in size, shape, and timing, resulting in an irregular, frequently rapid ventricular response. The irregularity of the heart rate and absence of the normal P wave are important features in detecting AFIB from the ECG signals. It is therefore desirable to provide a system and method for improved P wave detection that can be used alone or in combination with other methods to detect various cardiac conditions. A system according to invention principles addresses deficiencies of known systems to improve cardiac condition detection.

SUMMARY OF THE INVENTION

In a first embodiment, an apparatus that detects at least one characteristic associated with an input signal waveform representing an electrophysiological signal of a patient is provided. The apparatus includes an acquisition processor that acquires data representing a sequence of successive pulses of heartbeat of a patient and a computation processor electrically coupled to the acquisition processor. The computation processor, for each heartbeat pulse, identifies a portion of the input signal that may include the at least one characteristic and, for the identified portion of the input signal, measures a first and second feature associated therewith, calculates a composite feature value representing the likelihood that the at least one characteristic is present in the identified portion of the input signal and compares the calculated composite feature value to a classification threshold value. An output processor is electrically coupled to the computation processor that generates data indicating the presence of the at least one characteristic in response to a determination that the calculated composite feature value exceeds the classification threshold.

In another embodiment, a method of detecting at least one characteristic associated with an input signal waveform representing an electrophysiological signal of a patient is provided. The method includes acquiring, by an acquisition processor, data representing a sequence of successive pulses of heartbeat of a patient. A computation processor identifies, for each heartbeat, a portion of the input signal that may include the at least one characteristic. A first and second feature associated with the identified portion of the input signal is measured by the computation processor and a composite feature value representing a likelihood that the at least one characteristic is present in the identified portion of the input signal is calculated. The calculated composite feature value is compared to a classification threshold value. Data is generated by an output processor that is electrically coupled to the computation processor. The generated data indicates the presence of the at least one characteristic in response to a determination that the calculated composite feature value exceeds the classification threshold.

DETAILED DESCRIPTION

A system that detects the presence or absence of at least one characteristic from waveform data representing electrophysiological signals is provided. The waveform data is sensed by at least one sensor connected to a patient and processed by a data processor to generate the waveform data. The waveform data is representative of a predetermined time period. The waveform data includes a plurality of individual data samples and a set of data includes at least one individual data sample. The system advantageously detects the presence of absence of the at least one characteristic in respective ones of the plurality of data samples. By detecting the presence or absence of the at least one characteristic in each data sample, the system advantageously generates a composite value therefrom which may be used in supporting patient care.

To determine the presence or absence of the at least one characteristic within a respective individual sample, the system identifies a predetermined window of time where the at least one characteristic would occur of present. Waveform data within the predetermined may be analyzed to determine if any data contained within the predetermined window may be representative of the at least one characteristic. Candidate data representative of the at least one characteristic may be determined from an amplitude of a portion of waveform relative to a baseline value. The system advantageously determines if candidate data exists by selecting the portion of the waveform having a maximum amplitude relative to the baseline value. The system advantageously confirms whether or not the candidate data is in fact representative of the at least one characteristic by determining a first feature and a second feature associated with the candidate data and employing at least one type of pattern classification algorithm to generate a composite feature score representative of the first and second features. The composite feature score is compared to a threshold value and, if the composite feature score exceeds the threshold value, the system is able to advantageously confirm that the candidate data represents the at least one characteristic of the waveform.

In one embodiment, the system may also distinguish between different portions of the waveform data that may be within the predetermined time window in order to advantageously ensure that the correct portion of the waveform will be used in confirming whether or not the candidate data is representative of the at least one characteristic. This embodiment may be active when there is more than one peak within the predetermined window. Upon determining that a plurality of peaks are present in the portion of the waveform within the predetermined window, the system analyzes which peak should be considered the candidate data by selecting the one of the plurality of peaks having the greatest amplitude relative to the baseline and measuring a distance between the selected peak and a respective one of the peaks contained within a preceding data sample. If the measured is greater than a threshold distance, the system determines that the selected portion of the waveform is the candidate data to be further processed. If the measured distance is less than the threshold distance, the system selects a peak within the predetermined window having the next highest amplitude. The system calculates the distance between this peak and a peak within the preceding data sample and compares with the threshold to determine if the distance exceeds the threshold. This process is repeated for all possible candidate data points in the window until the calculated distance exceeds the threshold value. If the distance criteria is not met the system determines that the at least one characteristic is not present.

The system advantageously processes each data sample in the set of data samples to identify a frequency of the at least one data characteristic in the set of data samples and use the determined frequency to identify a percentage of data samples including the at least one characteristic. The system may advantageously process sets of data samples at least one of successively, randomly and at predetermined time periods. In another embodiment, the system may process data samples that include a rolling number of individual data samples in real time. For example, a first set of samples may include samples 1-30 and the second set of samples may include samples 2-31 and so on enabling real-time determination of the presence or absence of the at least one characteristic.

The system may further advantageously determine additional characteristic(s) of the set of waveform data and use the determined additional characteristic(s) with the presence or absence of the first characteristic to identify a clinical condition of the patient. A clinical condition may include any medical condition that requires treatment. In response to identifying a clinical condition, the system may advantageously administer at least one type of treatment to the patient to remedy the clinical condition.

Figure 2:
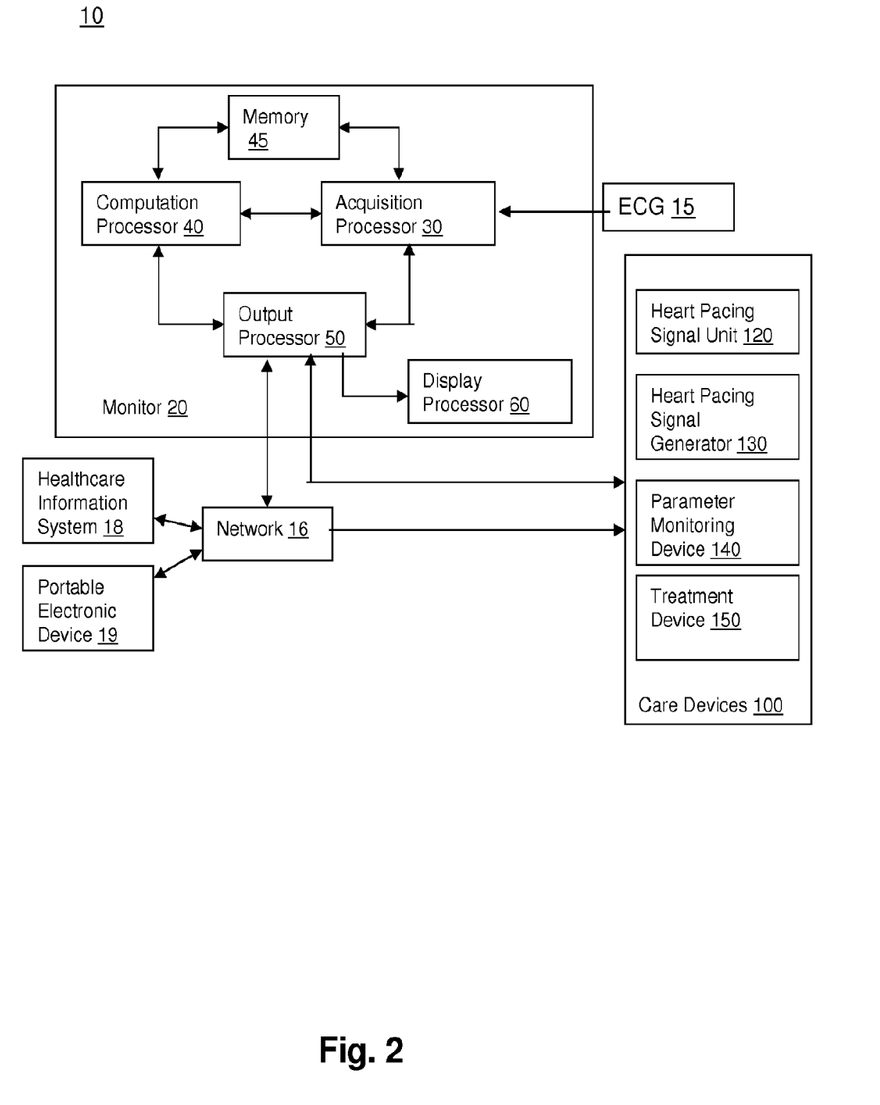
FIG. 2 is a block diagram of the characteristic detection system according to invention principles.

One embodiment of the characteristic detection system according to invention principles provides an improved system for detecting whether or not a waveform data representing a heartbeat of a patient includes a P-wave. An exemplary embodiment of the P-wave detection system, referred to generally by reference numeral 10, is depicted in FIG. 2. The system 10 receives ECG data 15 acquired from a patient. In one embodiment, the ECG data 15 may be received from an ECG monitor coupled to a patient via a plurality of sensors for sensing the electrophysiological signals representing a patient's heartbeat in real-time. In another embodiment, the received ECG data may be previously sensed ECG data that is stored in a device memory or in a repository of patient data. The ECG data 15 may be received by a monitoring device 20 that includes electronic circuitry conditioned to operate according to a predetermined algorithm for analyzing and detecting the presence or absence of a P-wave from the received set of ECG data. The monitoring device 20 may be any of a bedside patient monitoring device, a centralized monitoring station (e.g., a nursing station), or a combination of both. In another embodiment, the monitoring device 20 may include the electronic circuitry of an ECG monitor having the sensors connected directly thereto for sensing and processing heartbeat data of the patient. However, for ease of understanding, the system 10 according to invention principles will be described with respect to the processing of the ECG waveform that is one of currently being acquired or previously acquired. There is no further need to discuss the manner in which sensed electrophysiological signals are processed into an ECG waveform as this is not germane to the present inventive system.

Monitoring device 20 includes an acquisition processor 30 that is electrically coupled to received ECG waveform data 15 associated with at least one patient. Acquisition processor 30 acquires data representing individual heartbeat signals combined to generate a sequence of successive pulses of an electrical heartbeat waveform. Successively acquired data samples representing individual heartbeats are combined to generate a set of ECG data that is selectively analyzed by the monitoring device 20 to identify the presence or absence of a characteristic within the individual heartbeat data samples. In the presently described embodiment, the characteristic is the presence or absence of a P-wave in the individual heartbeat. The data representing a sequence of successive heartbeats may include any of the individual waves (e.g. P-wave, R-wave, T-wave and U-wave) and/or complexes (e.g. QRS complex) shown in the exemplary waveform of FIG. 1.

The monitoring device 20 further includes a computation processor 40 electrically coupled to acquisition processor 30. Computation processor 40 receives and processes the set of ECG data acquired by the acquisition processor 30. The computation processor 40 identifies at least one characteristic of individual heartbeats of the successive heartbeats that make up the set of ECG data. In this embodiment, the computation processor 40 selectively identifies the presence or absence of a P-wave in respective heartbeat waveforms by analyzing the acquired waveform and calculating at least two features associated therewith. The computation processor 40 processes the set of ECG data which represent a series of successive heartbeats over a predetermined time period (e.g., 30 beats) acquired by the acquisition processor 30 in order to generate a composite scoring value indicating the presence or absence of the at least one characteristic (P-wave) associated with the set of ECG data. The composite scoring value generated by the computation processor 40 advantageously provides a scoring metric that may be either indicative of a clinical condition or used in conjunction with other data to indicate a clinical condition that may require intervention or action by a healthcare provider (e.g. doctor, nurse, etc.).

For each heartbeat in the set of heartbeats, the computation processor identifies the R-wave of the heartbeat by selecting a portion of the waveform having a maximum amplitude (e.g. greatest peak relative to a baseline value). The peak of the R wave identified by the computation processor 40 is referred to as the fiducial time. Once the R-wave peak is identified, the computation processor 40 analyzes a section of the waveform within a window having a predetermined duration. The window identified by the computation processor begins at a predetermined time preceding the detected R-wave peak and has a predetermined duration. In one embodiment, the window begins at substantially 100 ms immediately preceding the peak of the R-wave and the window has a duration of substantially 200 ms.

The computation processor 40 analyzes the waveform within the predetermined time window to identify a candidate P-wave. A candidate P-wave represents a portion of the heartbeat waveform that is morphologically similar to a known P-wave and also occurs at substantially the same time in the waveform that a P-wave is known to occur. The computation processor 40 identifies candidate P-waves by measuring a peak of any waves that are present in the window relative to a baseline value (e.g., the isoelectric line of an ECG waveform) and selecting the candidate P-wave based on the measured wave having the highest peak (e.g., greatest amplitude). Should the computation processor 40 identify multiple candidate P-waves present in the window, the computation processor 40 applies selection criteria for selecting which of the plurality of potential candidate P-waves is in fact the candidate P-wave. The selection criteria applied by the computation processor 40 includes selecting, as the candidate P-wave, the wave having the greatest amplitude relative to the baseline value and which is positioned at a predetermined distance from the R-wave peak of the previous heartbeat. In one embodiment, if the potential candidate P-wave having the highest amplitude occurs more than substantially 320 ms after the peak of the previous R-wave (fiducial time), the computation processor 40 selects that wave as the candidate P-wave. If the potential candidate P-wave having the highest amplitude occurs less than substantially 320 ms from the fiducial time of the previous R-wave, the computation processor excludes that wave from being considered a candidate P-wave and selects the wave within the window having the next highest amplitude relative to the baseline that occurs later in time than the excluded wave. By using this selection criteria, the system advantageously excludes any T-waves of the previous heartbeat from being incorrectly selected as a candidate P-wave. In one embodiment, by excluding a wave having a high peak but appearing sooner than the predetermined distance from the peak of the previous R-wave, the system advantageously avoids selecting T-waves, especially those appearing before a premature atrial contraction (PAC) that appear in the P-wave candidate window. The computation processor 40 repeats this discrimination process until either a candidate P-wave is identified using the above criteria or it is determined that no wave in the window meets the above criteria indicating that no P-wave is present in the candidate window.

Figure 3A:
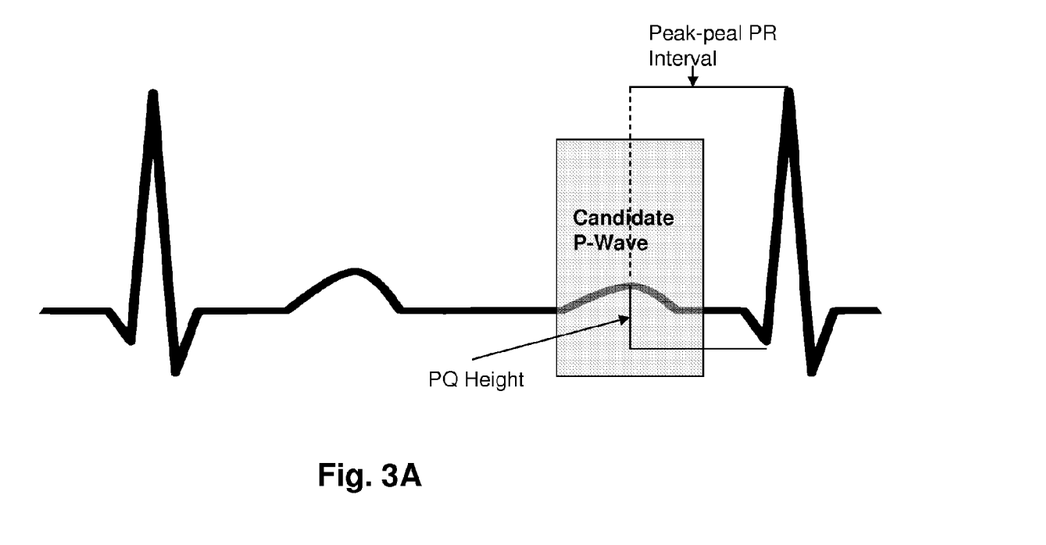
FIGS. 3A-3E are exemplary waveform diagrams showing cardiac waveform data and illustrating various features that may be used by a characteristic detection system according to invention principles.

In response to identifying the candidate P-wave, the computation processor 40 measures a first feature associated with the candidate P-wave. The first feature is calculated by comparing a portion of the candidate P-wave with a second portion of the heartbeat data occurs outside the predetermined window. In one embodiment, the first feature represents a height measured in millivolts between a highest peak of the candidate P-wave and a trough of the Q-wave of the QRS complex (e.g. PQ height). By calculating the height of the candidate P-wave, the computation processor 40 will later be able to differentiate between legitimate P-waves and other spurious peaks that may be associated with noise in the signal. The computation processor 40 further measures a second feature associated with the candidate P-wave. The second feature is measured by comparing a portion of the candidate P-wave with a third portion of the heartbeat data that occurs outside the predetermined window. In one embodiment, the second feature represents a time in milliseconds between the peak of the candidate P-wave and a peak of the R-wave within the individual heartbeat (e.g., peak-to-peak PR interval). The peak-to-peak PR interval is an advantageous feature because, in a normal sinus rhythm, the actual P-wave typically occurs relatively close to the peak of the R-wave of that heartbeat. Research has shown empirically that the PR interval of a legitimate P-wave is usually between 100 and 200 ms, though the PR interval may be longer in the presence of certain arrhythmias (e.g., atrioventricular blocks). A graphical depiction of the first and second features is shown in FIG. 3A. The computation processor 40 uses first feature data and second feature data for determining the composite characteristic score indicating that the candidate P-wave is more than likely an actual P-wave in the manner discussed below.

Figure 3B:
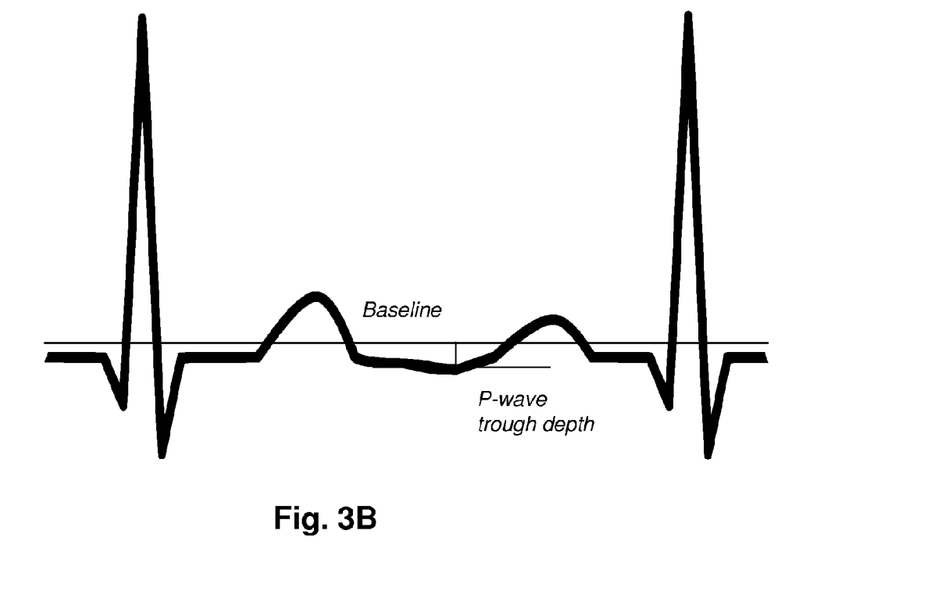
Figure 3C:
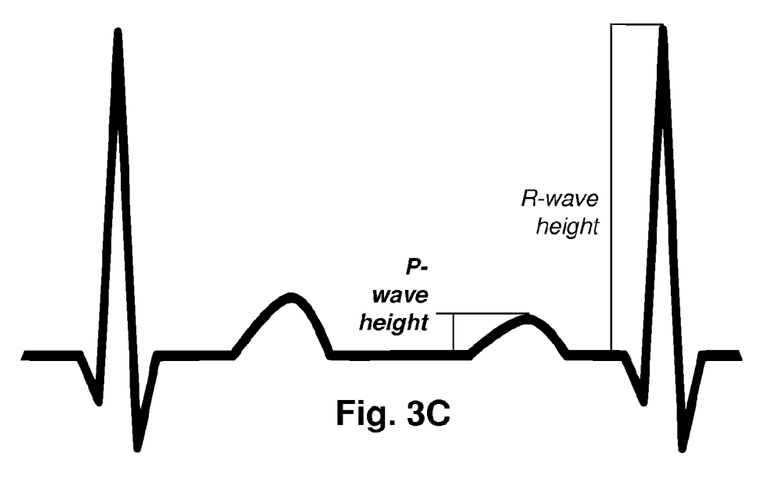
Figure 3D:
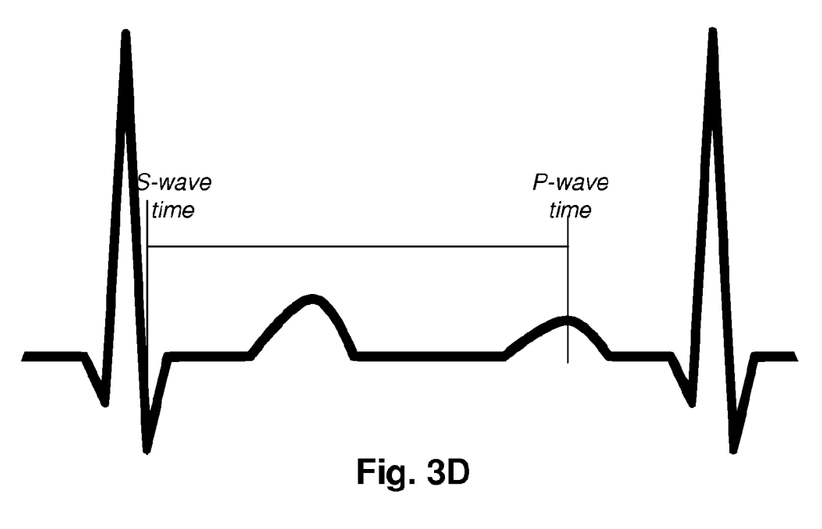
Figure 3E:
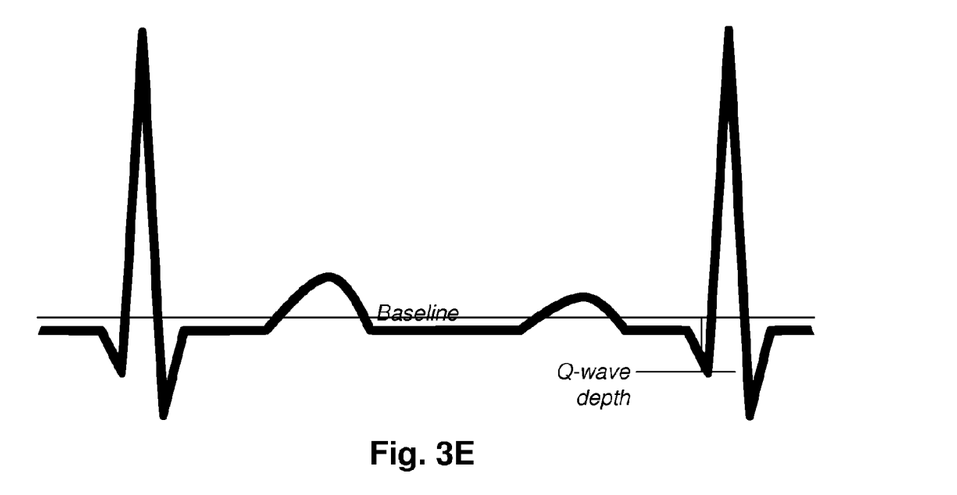

The above described first and second features are described for purposes of example only and the computation processor 40 may calculate other features associated with the candidate P-wave for determining composite characteristic score indicating whether it is more or less than likely that the candidate P-wave is an actual P-wave. For example, the first and second features calculated by the computation processor 40 may be selected from and measured according to the features in the various waveforms shown in FIGS. 3B-3E. One exemplary feature as shown in FIG. 3B is the depth of a trough that precedes the peak of the candidate P-wave. The depth is measured in millivolts relative to a baseline value. Another exemplary feature as shown in FIG. 3C is a ratio of the candidate P-wave amplitude to the R-wave amplitude of the same heartbeat wherein the amplitude is measured relative to the baseline isoelectric line in the waveform. A further feature is shown in FIG. 3D which represents a time measured in milliseconds between the peak of the candidate P-wave and the S-wave of the previous heartbeat. Yet another feature is shown in FIG. 3E which measures a depth of the Q-wave measured in millivolts relative to the baseline. These are merely examples of features associated with the candidate P-wave that may be used for determining the composite characteristic score. In practice, any measurement readily obtainable from the waveform may be used as a feature to detect a P-wave. Alternatively, while the computation processor 40 calculates the composite characteristic score from the first and second features, the composite characteristic score may also be calculated using more than two features of the candidate P-wave.

The computation processor 40 combines the first and second feature data associated with the candidate P-wave to generate a classification score that maps data associated with multivariable space (the first feature data and the second feature data) into a single variable space to determine on a beat-by-beat basis whether or not the candidate P-wave is an actual P-wave. This advantageously compresses a complex, multidimensional feature space into a single dimension. The computation processor 40 compares the calculated classification score associated with each beat to a threshold value. If the classification score for the candidate P-wave is greater than the threshold value, the computation processor 40 updates a memory 45 electrically coupled thereto with data representing the outcome of the threshold comparison indicating whether the candidate P-wave is or is not a P-wave.

The threshold value against which the classification score for the particular heartbeat is evaluated may be calculated using any pattern classification technique that enables the computation processor 40 to discriminate between respective classes of data. In this case, pattern classification technique allows the system 10 to discriminate whether the candidate P-wave is an actual P-wave or not a P-wave.

In one embodiment, the computation processor 40 calculates the classification score for the particular candidate P-wave using a linear discriminant analysis (LDA) algorithm. The aspects and parameters of an LDA algorithm are well known to those skilled in the art of pattern classification and any LDA algorithm able to successfully classify patterns and discriminate between multiple classes of data types may be employed by the computation processor. By using LDA, the computation processor 40 advantageously generates a vector of weights $\vec{w}$ including a first weight $w_1$ and a second weight $w_2$. The vector of weights $\vec{w}$, when multiplied with the first feature value and the second feature value, yields the classification score representing a single feature that best discriminates between normal beats with P-waves (one class) and those without (the other class). The classification score that best discriminates between the two classes is one in which samples from different classes are as distinct as possible, while samples from the same class are as similar as possible. The classification score is produced by multiplying the first feature data and second feature data by the vector of weights $\vec{w}$ and comparing the classification score to a threshold to see if the threshold is exceeded thereby indicating that the candidate P-wave is actually a P-wave. In this embodiment, the classification score (CS) may be calculated according to the following:

$$F_1(w_1) \times F_2(w_2) = CS \quad (1)$$

Wherein $F_1$ and $F_2$ are the first and second feature values and $w_1$ and $w_2$ are the weights representing the relative importance that the particular feature has in proving a candidate wave possesses the respective characteristic. In the embodiment, where the first feature is the PQ height, $w_1$ may be substantially 4.42 and where the second feature is the peak-peak PR interval, $w_2$ may be substantially 0.38. By solving Equation 1, the resulting classification score represents an LDA value that may be compared to a classification threshold (e.g. greater than or equal to −1.2).

It should be noted that, in order to use the classification score associated with respective candidate P-waves, the threshold that separates the two classes (e.g. P-wave and not a P-wave) needs to be properly determined. To determine the threshold, the first and second feature types used by the system are evaluated in a set of training data. In one embodiment, the training data used by the system 10 to derive the classification threshold may be ECG data from the MIT-BIH Arrhythmia Database. The MIT-BIH database is a publicly available database that includes 24 hours of data spread across 48 records, each checked for a variety of arrhythmias by expert clinicians on a per-beat basis. Among the arrhythmias included are 2.5 hours of AFIB and AFL, spread across 151 episodes and eight records. The system evaluates the first feature and second feature against the data in the training set to determine the proper weighting to be associated with each of the first feature and second feature such that the respective weight applied to the respective feature is based on which feature data better discriminates between the two classes.

An LDA algorithm using the selected features of PQ height (first feature) and peak-peak PR interval (second feature) maximizes a distance between the mean values of the two classes while minimizing the standard deviation of values from within each class. The statistical distance between the means of each feature is measured by the between-class scatter matrix, $S_B$ calculated according to the following:

$$S_B = (\vec{m}_1 - \vec{m}_2)(\vec{m}_1 - \vec{m}_2)^T \quad (2)$$

where $\vec{m}_1$ and $\vec{m}_2$ are the sample means for each of the respective classes and T is the matrix transpose operation. To measure the standard deviations of each class, we compute the scatter matrices $S_1$ and $S_2$:

$$S_i = \sum_{\vec{x} \in D_i} (x - \vec{m}_i)(x - \vec{m}_i)^T \quad (3)$$

where $D_i$ represents the subset of samples in the ith class. The two scatter matrices are then combined to form the within-class scatter matrix, $S_w$:

$$S_w = S_1 + S_2 \quad (4)$$

We can now define a criterion function $J(\vec{w})$ in terms of these matrices:

$$J(w) = \frac{\vec{w}^T S_B \vec{w}}{\vec{w}^T S_W \vec{w}} \quad (5)$$

The vector $\vec{w}$ that maximizes this criterion function is the linear discriminant, and can be found by solving the generalized eigenvalue problem.

$$S_B \vec{w} = \lambda S_w \vec{w} \quad (6)$$

Thus, the LDA algorithm advantageously compresses a complex, multi-dimensional feature space into a single dimension. Moreover, this enables new vectors of features to be easily transformed into this space by applying simple vector multiplication $\vec{w}^T \vec{x}$.

Figure 4:
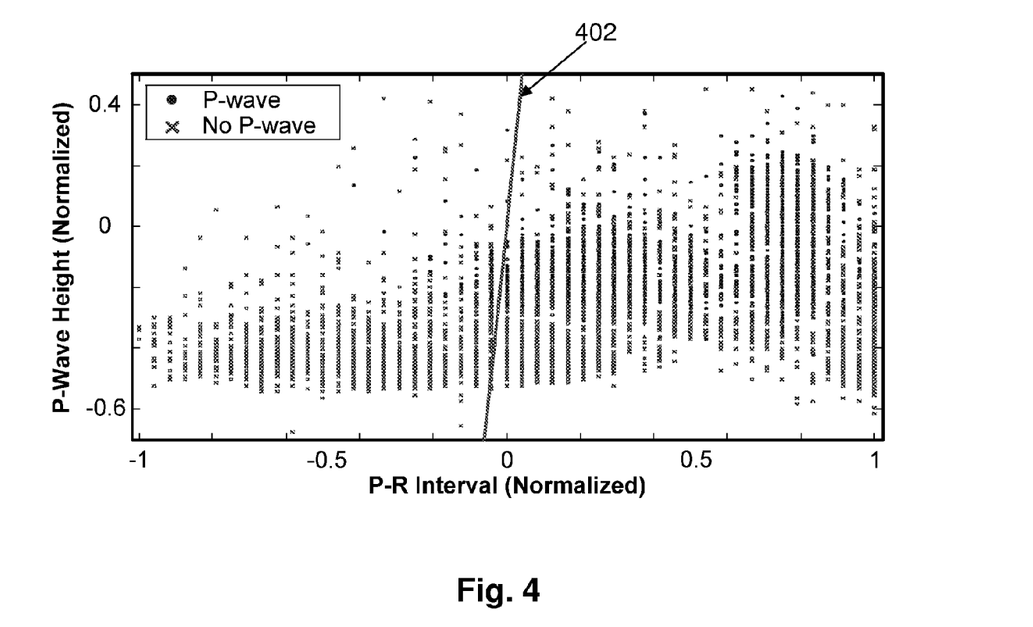
FIG. 4 is a scatter plot graph depicting characteristics detected by the characteristic detection system according to invention principles.
Figure 5:
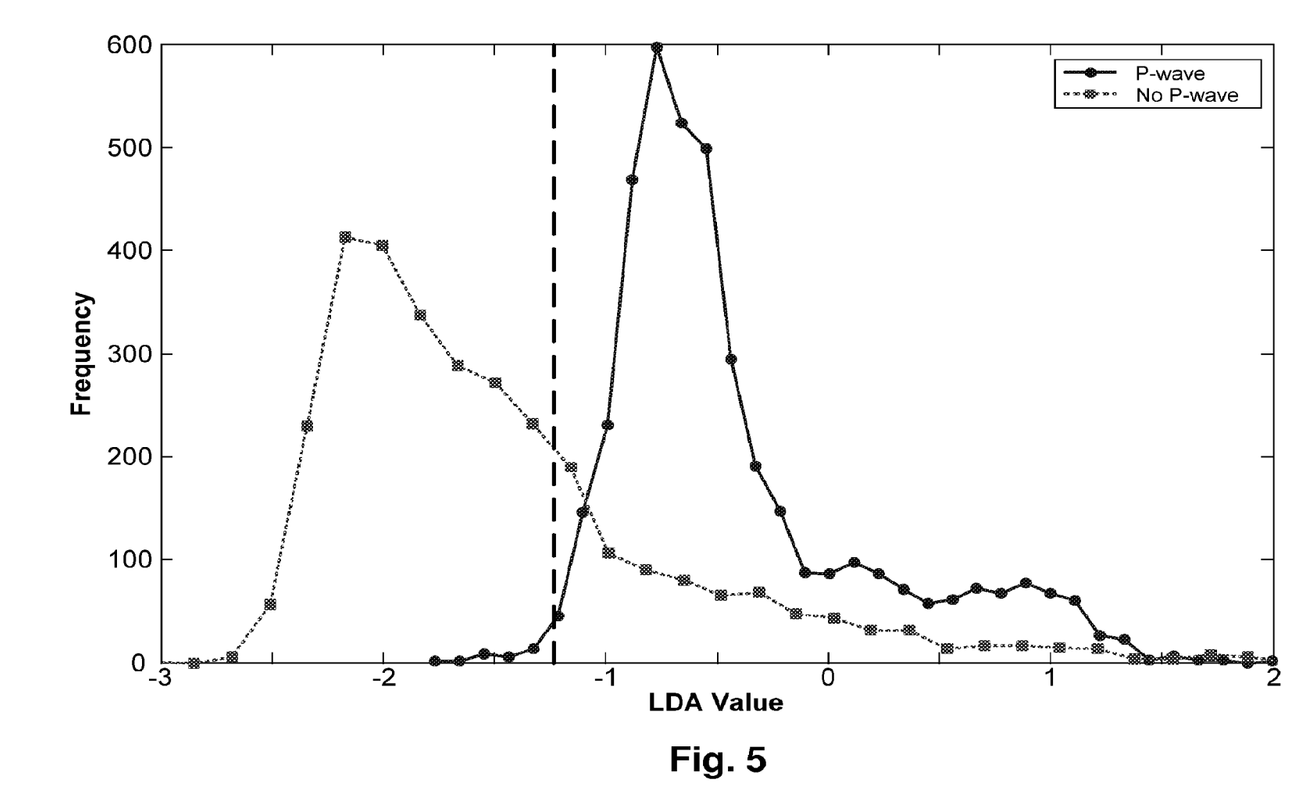
FIG. 5 is a graphical depiction of the threshold against which feature data is compared to detect a characteristic in the characteristic detection system according to invention principles.

In exemplary practice, the generation of the classification threshold used by the computation processor 40 can be visualized in FIGS. 4 and 5. An exemplary scatter plot of the combined scatter matrix $S_w$ is shown in FIG. 4. The scatter matrix $S_w$ includes the P-wave detection features applied to the set of training data. The relationship of the features is projected onto the single dimension represented by the solid line labeled 402. In this example, a feature space consisting of two dimensions (peak-peak PR interval and PQ height) that describes two classes of beats (those with P-waves and those without) is shown. Thus, in FIG. 4, the scatter plot allows for some distinction to be made between those beats with P-waves and those without. By applying LDA to the data in the scatter plot of FIG. 4, the result is a single feature made by linearly combining the first feature data and the second feature data according to a relative strength of each feature in discriminating between the two classes. The single combined feature may be plotted as a probability density showing the likelihood that a particular wave is or is not a P-wave. FIG. 5 is an exemplary plot of probability density functions for each of the two classes (e.g. P-wave and not a P-wave). Using a Bayesian maximum likelihood classifier, the data plotted in FIG. 5 can be separated into two distinct classes at a single value represented in this figure by the dotted vertical line. Thus, the dotted vertical line in FIG. 5 represents the classification threshold against which any LDA values associated with candidate P-waves can be compared to determine whether not the candidate P-wave is more or less likely or not to be an actual P-wave. As shown herein, a candidate P-wave is more likely to be an actual P-wave if the classification score has an LDA value greater than or equal to −1.2.

The implementation of the LDA algorithm by the computation processor 40 to calculate the classification score and compare the calculated score to the corresponding classification threshold is described for purposes of example only. The system 10 may use any other pattern classification algorithm to combine the multiple data values into a single composite data value representing a classifier identifying the class to which the combined data belongs. Other exemplary pattern classification algorithms may include algorithms based on any of neural networks, support vector machines, or hidden Markov models. Alternatively, the pattern classification algorithm may combine any of the individual pattern classification algorithms.

Referring back to FIG. 2, the computation processor 40 analyzes the candidate P-waves for each heartbeat in the set of heartbeat data and updates the memory 45 with the number of actual P-waves determined to be present. The computation processor 40 may process the number of candidate P-waves identified to be actual P-waves for use in determining if a clinical condition exists. For example, the computation processor 40 may determine a percentage of heartbeats in the set of heartbeats in which a valid P-wave was detected. The determined percentage of P-waves present can be used alone or in combination with another characteristic associated with the waveform data to determine if a clinical condition is present. In one embodiment, the P-wave detection system may be used for beat classification of heartbeats to determine if the heartbeat data sensed by the monitoring device has a normal sinus rhythm associated therewith or if there is one of premature atrial contraction (PAC) or supraventricular tachycardia (SVT). In another embodiment, the P-wave detection system may be used in conjunction with another characteristic of the ECG waveform to determine if a patient is suffering atrial fibrillation (AFIB).

While the above description of system operation centers around detecting a characteristic of a respective heartbeat from a set of heartbeats, the system advantageously detects the presence or absence of the characteristic for all heartbeats in the set of heartbeat data. In another embodiment, the system 10 continually detects whether or not the characteristic (P-wave) is present in every heartbeat. In this embodiment, the computation processor 40 can begin the continuous characteristic detection once an initial set of heartbeat data is acquired by the acquisition processor 30 because the presence or absence of the characteristic is clinically significant over a period of time.

Output processor 50 is electrically connected to each of acquisition processor 30 and computation processor 40. Output processor 50 is conditioned to generate data representing message data that includes information about the characteristics determined to be present in one of (a) an individual heartbeat; (b) the set of heartbeat data processed by the computation processor 40; and (c) a subset of a plurality of heartbeats selected from the set of heartbeat data. The message data generated by the output processor may provide information regarding the number of P-waves determined to be present in the set of data. In another embodiment, the message data may include information that the patient is experiencing a clinical condition as determined by the number of P-waves present in the set of data. Message data may also include patient identifier information including data representing at least one of (a) patient name, (b) patient ID number and (c) patient location information. Message data generated by output processor 50 may be communicated to a destination system, for example a healthcare information system 18 and/or a portable electronic device 19 (e.g. PDA, cell phone, mobile computing device, etc.). Message data communicated to destination system is used for providing real-time monitoring of the particular patient by a healthcare professional. Message data received by the destination system may be parsed and used to automatically update a patient healthcare record.

Output processor 50 is also conditioned to generate control data responsive to the message data for controlling at least one patient care device 100. Patient care devices include, for example, a heart pacing signal unit 120, heart pacing signal generator 130, patient parameter monitoring device 140 and patient treatment device 150. Control data generated by output processor 50 in response to an alert message may also be communicated to at least one of the heart pacing signal generator 130 and the heart pacing signal unit 120 for automatically initiating generation of a heart pacing signal in response to the alert message or for automatically providing a heart pacing signal to a patient heart in response to the alert message. In another embodiment, control data generated by output processor 50 in response to the message data may also be communicated to patient parameter monitoring device 140 for automatically changing monitoring device operational settings (e.g., changing the settings of an ECG monitoring device). Output processor 50 may also generate control data in response to message data for controlling the patient treatment device 150 and automatically change operational settings and/or treatment provided to a patient. Treatment device 150 includes, for example, an infusion pump for controlling delivery of at least one medication to a patient or a ventilator. It should be noted that treatment device 150 may include any device that is coupled to a patient and used to provide healthcare related services to the patient.

The monitor 20 may also be connected to at least one type of destination system, for example, healthcare information system 18 and/or portable electronic devices 19, via network 16. Network 16 is preferably adapted to use one or more data formats, otherwise called protocols, depending on the type and/or configuration of the various elements in system 10. Examples of the information system data formats include, without limitation, an RS232 protocol, an Ethernet protocol, a Medical Interface Bus (MIB) compatible protocol, DICOM protocol, an Internet Protocol (IP) data format, a local area network (LAN) protocol, a wide area network (WAN) protocol, an IEEE bus compatible protocol, and a Health Level Seven (HL7) protocol, HTTP and HTTPS. Network communication paths may be formed as a wired or wireless (W/WL) connection. The wireless connection permits a person using system 10 to be located at a distance beyond that permitted with a wired connection. Alternatively, a workstation may be directly connected to any of the destination systems and/or care devices using either wired or wireless communication networks and/or protocols.

Figure 6:
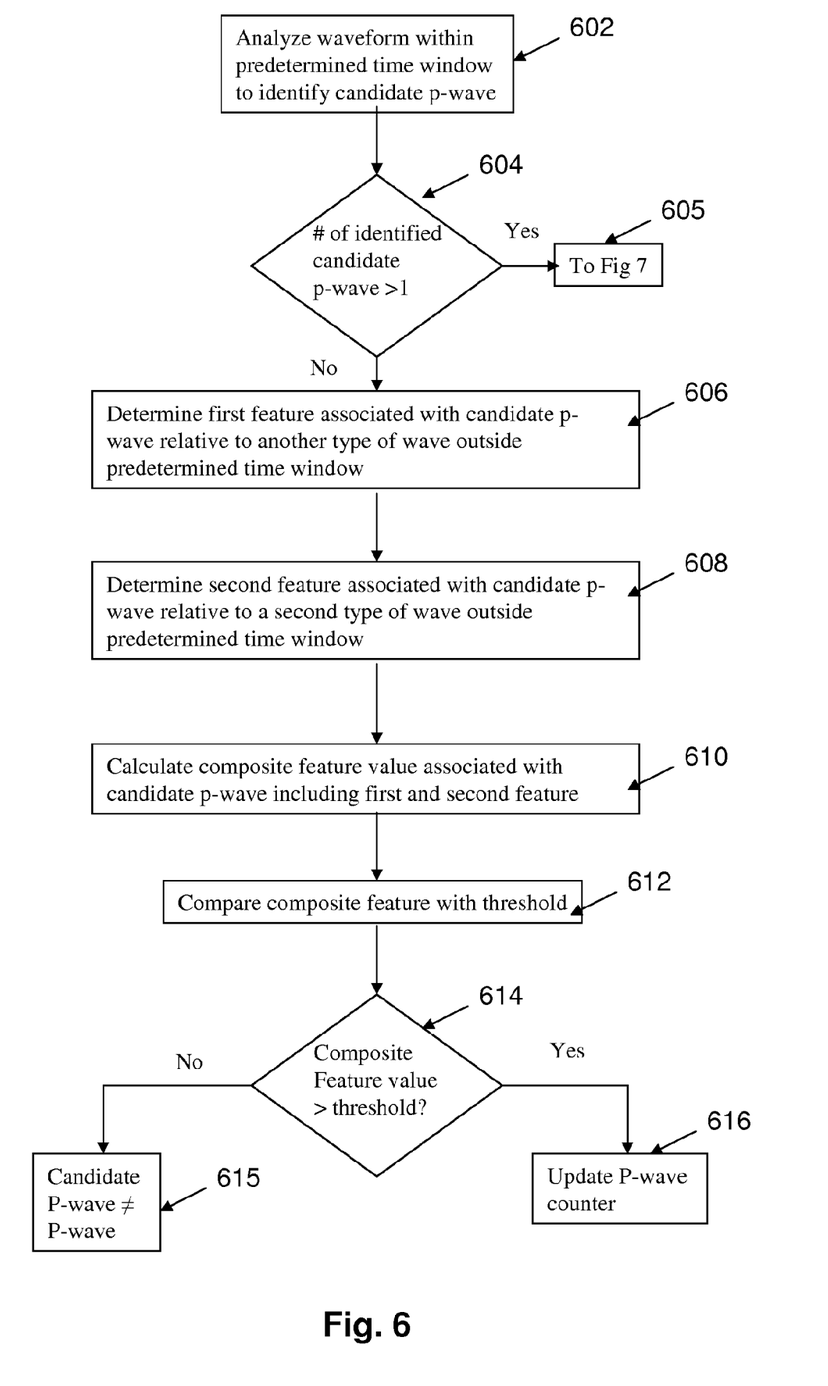
FIGS. 6-8 are flow diagrams representing algorithms implemented by the characteristic detection system according to invention principles.
Figure 7:
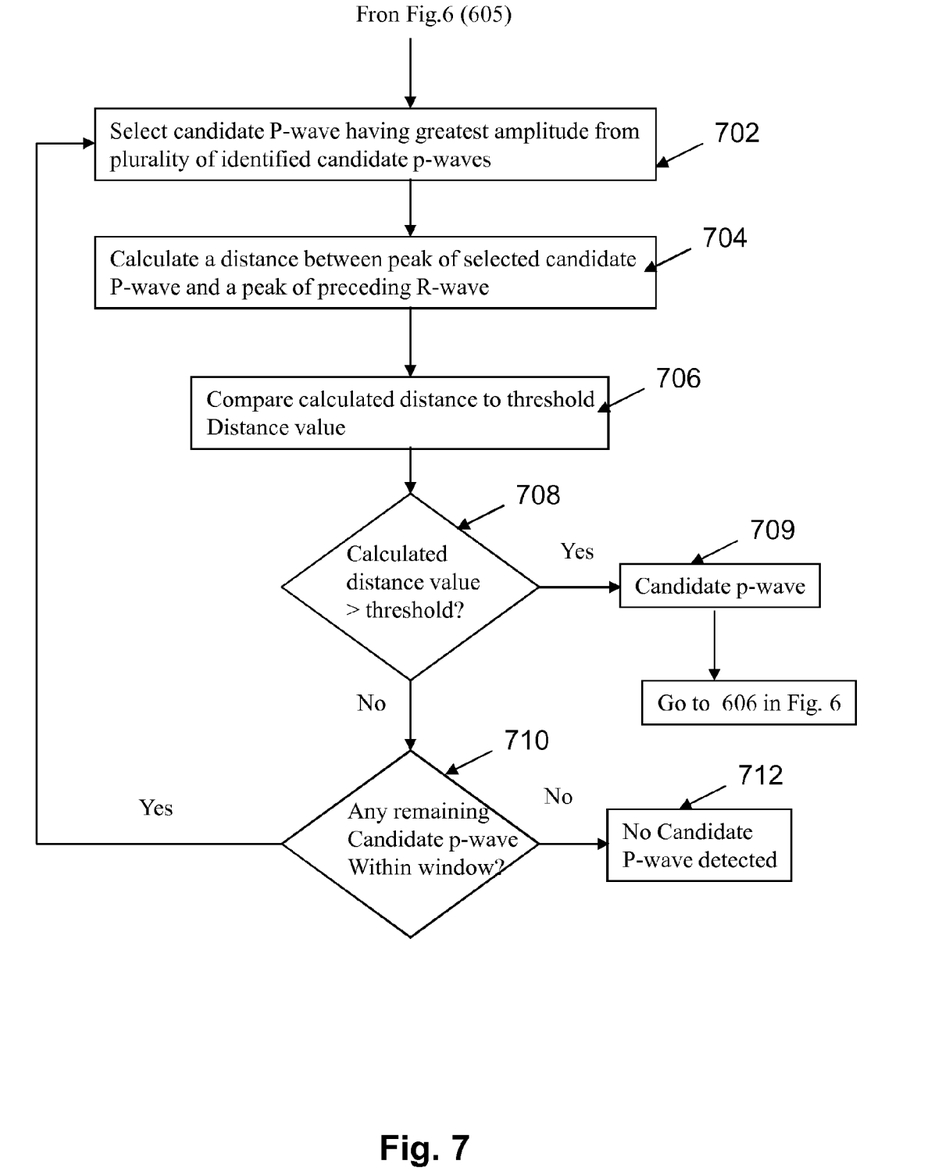

FIGS. 6 and 7 are flow diagrams detailing the operation of an exemplary characteristic detection algorithm that is able to detect whether or not a particular characteristic is present within a signal by using at least two feature associated with the portion of the signal at which the characteristic is typically located. The algorithms shown and described with respect to FIGS. 6 and 7 may be implemented by the computation processor 40 shown in FIG. 2.

Referring now to FIG. 6, the following algorithm is described with respect to the analysis of a part of an input signal including a single heartbeat. However, this is for purpose of ease of understanding and the algorithm is repeated on all segments of the signal that include heartbeat data. Execution of the algorithm by the computation processor 40 occurs in response to receiving an input signal having a predetermined signal length and including a predetermined number of individual heartbeats. In one embodiment, the predetermined length of the input signal is substantially 30 seconds and the predetermined number of individual heartbeats within the input signal is 30. This advantageously enables the system to determine whether or not the presence or absence of a particular characteristic is of any clinical significance. For example, if the characteristic is determined to be present in a predetermined percentage of individual beats within the input signal, the system 10 may use this information to generate a message indicative of the identified clinical condition.

In step 602, where the characteristic being detected by the system is the presence or absence of a P-wave in individual heartbeats, a portion of the waveform associated with an individual heartbeat that is within a predetermined time window is analyzed to identify any peaks representative of a candidate P-wave. The system identifies a candidate P-wave by identifying the portion of the signal within the window having the maximum peak (e.g., highest amplitude). While analyzing the predetermined time window, the computation processor 40 determines if there are multiple peaks indicative of more than one candidate P-wave in step 604. By detecting multiple peaks present in the predetermined window, the computation processor 40 determines that there is more than one portion of the signal that needs to be analyzed in order to determine which peak, if any, actually represents a P-wave. If there is more than one peak present in the predetermined time window, the algorithm needs to identify which peak is the actual candidate P-wave and proceeds with the algorithm discussed hereinbelow with respect to FIG. 7.

If the query in step 604 yields a negative response indicating that the predetermined time window includes a single peak indicative of a candidate P-wave, the algorithm proceeds to step 606 to validate whether the candidate P-wave is an actual P-wave. In step 606, the computation processor 40 measures a first feature associated with the candidate P-wave. The first feature of the candidate P-wave is measured relative to a first type of wave of the same heartbeat signal that is outside of the predetermined time window. For example, the first feature associated with the candidate P-wave and measured by the computation processor 40 is an amplitude of the candidate P-wave relative to a trough of a Q-wave in the same heartbeat. In step 608, the computation processor 40 measures a second feature associated with the candidate P-wave. The second feature of the candidate P-wave is measured relative to a second type of wave of the same heartbeat signal that is outside of the predetermined time window. For example, the second feature is a time in milliseconds between a peak of the identified candidate P-wave and a peak of the subsequent R-wave in the same heartbeat signal.

In response to measuring the first and second features in steps 606 and 608, respectively, a composite feature value representing a classification score that includes the first and second feature data associated with the candidate P-wave is calculated in step 610. In one embodiment, the composite feature value may be a scalar value that is calculated by multiplying the data representing the first feature by a first weight value to obtain a weighted first feature value and multiplying the data representing the second feature by a second weighted value to obtain a weighted second feature value. The first and second weight values represent a relative importance that the respective feature has in determining whether or not the characteristic being detected is actually present in the portion of the signal. For example, if the first feature value is more important in discriminating between the candidate P-wave being an actual P-wave than the second feature value, then the first weight value would be greater than the second weight value. The computation processor 40 adds the first weighted feature value to the second weighted value to obtain the composite feature value representative of a classification score. The composite feature value is compared with a classification threshold which advantageously determines if the candidate P-wave is an actual P-wave in step 612. In step 614, the computation processor 40 determines if the composite feature value is greater than the threshold value. If the determination in step 614 is negative, then the system determines that the candidate P-wave is not an actual P-wave. In contrast, if the determination in step 614 is positive, then the computation processor 40 updates a characteristic counter in step 616 to indicate that the analyzed portion of the signal including the present heartbeat includes a P-wave.

FIG. 7 is a flow diagram detailing a portion of the algorithm that follows from the positive determination made in step 604 of FIG. 6 whereby the portion of the input signal within the predetermined time window may include more than one candidate P-wave requiring the system to select one of these waves as the candidate P-wave for further processing. In step 702, the computation processor 40 selects a first potential candidate P-wave by identifying a peak within the window having the greatest amplitude relative to a baseline value. A distance in time between a peak of the first potential candidate P-wave and a peak of a second type of waveform from a preceding heartbeat is calculated in step 704. For example, the distance between a peak of the first potential candidate P-wave and a peak of the preceding R-wave is calculated in milliseconds. The calculated distance is compared to a threshold distance value in step 706 and the system determines if the calculated distance is greater than the threshold value in step 708. The determination in step 708 advantageously enables the system to discriminate legitimate P-waves from T-waves of the prior heartbeat, especially the T-waves that may occur before a premature atrial contraction (PAC). If the determination in step 708 is positive, the system, in step 709, identifies the first potential candidate P-wave as the candidate P-wave and the algorithm reverts back to step 606 in FIG. 6 to confirm whether or not the candidate P-wave represents an actual P-wave. If the determination in step 708 is negative, a further determination is made in step 710 that checks if any further peaks within the predetermined time window are potential candidate P-waves. If the determination in step 710 is negative, the system indicates that no candidate P-waves are present, information regarding the current heartbeat being analyzed is updated and the algorithm reverts back to step 602 in FIG. 6 in order to analyze subsequent heartbeat data. If the determination in step 710 is positive, the algorithm reverts back to step 702 to determine if the next potential candidate P-wave is an actual candidate P-wave by selecting the peak within the window with the next greatest amplitude relative to baseline and which occurs later in time than the first potential candidate P-wave and measure the distance in time between this potential candidate P-wave and the R-wave of the preceding heartbeat.

Referring back to FIG. 2, the characteristic detection system may also detect a second characteristic of an input signal and use information associated with the first and second characteristics in order to detect a condition of the patient. In one embodiment, where the characteristic detection system detects the presence or absence of P-waves, the system may also detect another characteristic of the input signal representing a series of successive heartbeats in order to detect atrial fibrillation (AFIB) in a patient. In this embodiment, the computation processor 40 may process the acquired ECG data in order to calculate a measurement describing the RR interval variability between successive heartbeats. For example, the computation processor may calculate a pulse interval irregularity measure based on a sum of time interval differences occurring between pairs of successive pulses of the sequence of successive pulses. Time interval differences exceeding a predetermined maximum threshold (at least 290 ms) are excluded from the sum and a calculated pulse interval irregularity measure is compared with a predetermined irregularity measure threshold. This manner of calculating the RR interval variability as the second characteristic is described for purposes of example only and any manner of calculating the RR interval variability may be used by the system 10.

By detecting the second characteristic representing the RR interval variability, the system is able to advantageously quantify the irregularity of an underlying heartbeat. The irregularity of the underlying heartbeat is known to be indicative of AFIB. However, if only this second characteristic was used to detect AFIB, the result would include too many false positives. Thus, the system advantageously employs the P-wave detection algorithm to reduce the number of false positive indications of AFIB by measuring a percentage of heartbeats with a set of ECG data acquired by the acquisition processor 30 to measure the irregularity of the atrial activity.

Figure 8:
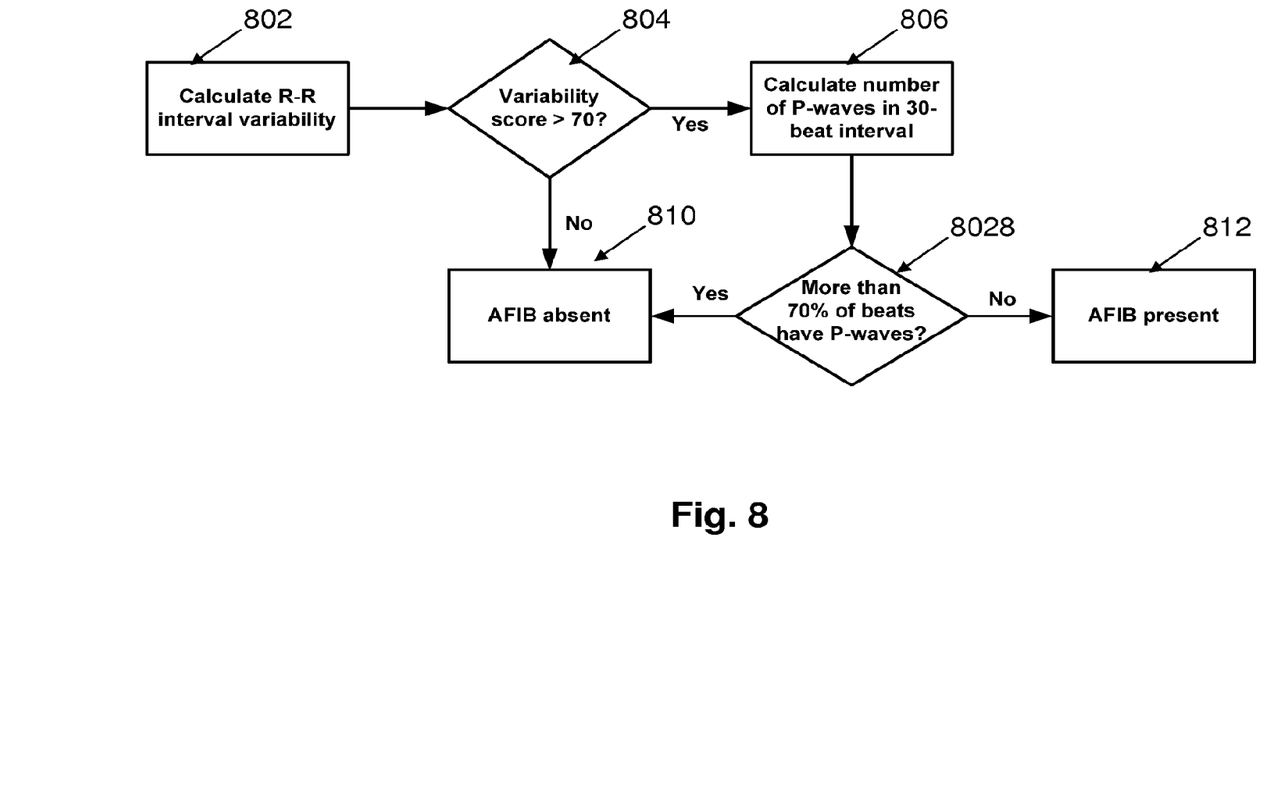

FIG. 8 represents an algorithm that employs the P-wave detection described above with RR irregularity measurement that is common to many AFIB detection systems. As RR irregularity is the primary manner in which AFIB detection occurs, the RR interval variability is calculated in step 802. In step 804 a determination is made to determine if there is RR interval irregularity in a certain percentage beats in the set of heartbeat data. If the percentage of beats having RR irregularity is greater than a threshold, the p-wave detection algorithm described in FIGS. 6 and 7 above is executed, in step 806, by the computation processor 40 to detect the presence or absence of P-waves in the same set of heartbeat data. In step 808, the computation processor 40 may query the memory 45 to identify a number of heartbeats in the set of heartbeats that have been determined to include actual P-waves and computes a percentage of beats that include P-waves. If the percentage of heartbeats that include P-waves exceeds a threshold value, the system determines that AFIB is absent in step 810 and normal patient monitoring continues. If the determination in step 808 is negative, the computation processor 40 determines that AFIB is present and signals the output processor 50 to generate message data indicating that AFIB is present thereby enabling a clinician to provide care to the patient.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An apparatus that detects at least one characteristic associated with an input signal waveform representing an electrocardiograph (ECG) signal of a patient, the at least one characteristic being detected by the apparatus is the presence of a P-wave, the apparatus comprising:
   an acquisition processor that acquires data representing a sequence of successive pulses of heartbeat of a patient;
   a computation processor electrically coupled to said acquisition processor that, for each heartbeat pulse,
      identifies a portion of the input signal that may include the at least one characteristic and, for the identified portion of the input signal, measures a first and second feature associated therewith the identified portion of the input signal representing a candidate P-wave, wherein the portion of the input signal identified by the computation processor is within a window of time occurring at a predetermined time prior to an R-wave of a same heartbeat pulse;

in response to detecting a plurality of peaks within the window, selects one of the plurality of peaks as candidate data representative of the presence of the at least one characteristic;

selects a first peak of the plurality of peaks having the greatest amplitude;

measures a distance between the first peak and a peak of an R-wave of a preceding heartbeat waveform;

compares the measured distance to a predetermined threshold, wherein the selected first peak is identified as the candidate data when the measured distance exceeds the predetermined threshold;

calculates a composite feature value using the first and the second feature, the composite feature value representing the likelihood that the at least one characteristic is present in the identified portion of the input signal;

compares the calculated composite feature value to a classification threshold value; and an output processor electrically coupled to said computation processor that generates data indicating the presence of the P-wave in response to a determination that the calculated composite feature value exceeds the classification threshold.

2. The apparatus according to claim 1, wherein the computation processor selects as candidate data representative of the at least one characteristic, a peak of the input signal waveform within the window having a greatest amplitude and measures the first and second features of the candidate data of the peak.

3. The apparatus according to claim 1, wherein in response to determining that the measured distance is less than the predetermined threshold, the computation processor selects a peak within a window having a next highest amplitude and occurring subsequent to the first peak; measures a distance between the peak having the next highest amplitude with the predetermined threshold, wherein the peak having the next highest amplitude is identified as the candidate data when the measured distance exceeds the predetermined threshold.

4. The apparatus according to claim 1, wherein the first feature measured by the computation processor represents a height of a peak of the identified portion of the waveform and a trough of a subsequently occurring wave of the heartbeat waveform, and the second feature measured by the computation processor represents a time between a peak of the identified portion of the waveform and a peak of a second subsequently occurring wave of the heartbeat waveform.

5. The apparatus according to claim 1, wherein the computation processor measures the first feature by determining a height of a peak of the candidate P-wave above a trough of a Q-wave of a same heartbeat, and measures the second feature by determining a time between a peak of the candidate P-wave and a peak of the R-wave of the respective heartbeat.

6. The apparatus according to claim 1, wherein the computation processor calculates the composite feature value by multiplying data representing the first feature by a first weight value of a weighting vector and multiplies data representing the second feature by a second weight value of the weighting vector.

7. The apparatus according to claim 6, wherein the weighting vector includes weight values that correspond to respective strengths associated with the ability of each of the first and second features to successfully identify the presence of the at least one characteristic in the identified portion of the waveform.

8. The apparatus according to claim 1, wherein the computation processor selects the classification threshold value by classifying a pattern within a set of training data that includes a heartbeat waveform having the at least one characteristic.

9. The apparatus according to claim 1, wherein the computation processor identifies a further characteristic associated with the input signal, and uses the presence of the P-waves in the respective heartbeats of the successive heartbeats in conjunction with the identified further characteristic to determine if the patient is experiencing a cardiac condition.

10. The apparatus according to claim 9, wherein the further characteristic is a pulse irregularity measurement of heartbeats in the successive pulses of heartbeat data, wherein the computation processor calculates a pulse interval irregularity measure based on a sum of time interval differences occurring between pairs of successive pulses of said sequence of successive pulses and a mean time interval of successive pulses of said sequence and excluding time interval differences exceeding a predetermined maximum threshold from said sum.

11. The apparatus according to claim 10, wherein the computation processor calculates a P-wave presence indicator by determining a percentage of heartbeats in the successive heartbeats having P-waves, and compares the determined pulse irregularity value to a first threshold value and the P-wave presence indicator to a second threshold value, the cardiac condition is determined to be present if the pulse irregularity value exceeds the first threshold and the P-wave presence indicator is below the second threshold value.

12. A method of detecting at least one characteristic associated with an input signal waveform representing an electrocardiogram (ECG) signal of a patient, the at least one characteristic being detected is the presence of a P-wave, the method comprising the activities of:

acquiring, by an acquisition processor, data representing a sequence of successive pulses of heartbeat of a patient;

identifying, by a computation processor, for each heartbeat, a portion of the input signal that may include the at least one characteristic, the identified portion of the input signal representing a candidate P-wave, wherein the portion of the input signal identified by the computation processor is within a window of time occurring at a predetermined time prior to an R-wave of a same heartbeat pulse;

selecting one of the plurality of peaks as candidate data representative of the at least one characteristic in response to detecting a plurality of peaks within the window;

selecting a first peak of the plurality of peaks having the greatest amplitude;

measuring a distance between the first peak and a peak of an R-wave of a preceding heartbeat waveform;

comparing the measured distance to a predetermined threshold;
identifying the selected first peak as the candidate data when the measured distance exceeds the predetermined threshold;
measuring a first and second feature associated with the identified portion of the input signal;
calculating a composite feature value using the first and the second feature, the composite feature value representing a likelihood that the at least one characteristic is present in the identified portion of the input signal;
comparing the calculated composite feature value to a classification threshold value; and
generates, by an output processor electrically coupled to the computation processor, data that indicates the presence of the P-wave in response to a determination that the calculated composite feature value exceeds the classification threshold.

13. The method according to claim 12, further comprising the activities of
selecting, by the computation process, as candidate data representative of the at least one characteristic, a peak of the input signal waveform within the window having a greatest amplitude; and
measuring the first and second features of the candidate data of the peak.

14. The method according to claim 12, wherein
selecting selects a peak within a window having a next highest amplitude and occurring subsequent to the first peak in response to determining that the measured distance is less than the predetermined threshold, measuring a distance between the peak having the next highest amplitude and a peak of an R-wave of a preceding heartbeat waveform
comparing the measured distance of the next highest peak with the predetermined threshold,
identifying the peak having the next highest amplitude as the candidate data when the measured distance exceeds the predetermined threshold.

15. The method according to claim 12, wherein the activity of measuring further includes
measuring the first feature representing a height of a peak of the identified portion of the waveform and a trough of a subsequently occurring wave of the heartbeat waveform, and
measuring the second feature representing a time between a peak of the identified portion of the waveform and a peak of a second subsequently occurring wave of the heartbeat waveform.

16. The method according to claim 12, further comprising the activities of
measuring the first feature by determining a height of a peak of the candidate P-wave above a trough of a Q-wave of a same heartbeat, and
measuring the second feature by determining a time between a peak of the candidate P-wave and a peak of the R-wave of the respective heartbeat.

17. The method according to claim 12, further comprising the activity of
calculating the composite feature value by multiplying data representing the first feature by a first weight value of a weighting vector and multiplies data representing the second feature by a second weight value of the weighting vector.

18. The method according to claim 17, wherein the weighting vector includes weight values that correspond to respective strengths associated with the ability of each of the first and second features to successfully identify the presence of the P-wave in the identified portion of the waveform.

19. The method according to claim 12, further comprising the activity of
selecting the classification threshold value by classifying a pattern within a set of training data that includes a heartbeat waveform having the at least one characteristic.

20. The method according to claim 12, further comprising the activities of
identifying a further characteristic associated with the input signal; and
using the presence of the P-waves in the respective heartbeats of the successive heartbeats in conjunction with the identified further characteristic to determine if the patient is experiencing a cardiac condition.

21. The method according to claim 20, wherein
the further characteristic is a pulse irregularity measurement of heartbeats in the successive pulses of heartbeat data, and further comprising
calculating a pulse interval irregularity measure based on a sum of time interval differences occurring between pairs of successive pulses of said sequence of successive pulses and a mean time interval of successive pulses of said sequence and excluding time interval differences exceeding a predetermined maximum threshold from said sum.

22. The method according to claim 21, further comprising
calculating a P-wave presence indicator by determining a percentage of heartbeats in the successive heartbeats having P-waves,
comparing the determined pulse irregularity value to a first threshold value and the P-wave presence indicator to a second threshold value; and
determining that the cardiac condition is present if the pulse irregularity value exceeds the first threshold and the P-wave presence indicator is below the second threshold value.

* * * * *